United States Patent [19]
Gajda

[11] Patent Number: 6,153,806
[45] Date of Patent: Nov. 28, 2000

[54] MINIMIZING DIPHENYLETHANE FORMATION IN ALKYLATION OF BENZENE BY ETHYLENE CATALYZED BY ZEOLITE BETA

[75] Inventor: Gregory J. Gajda, Mt. Prospect, Ill.

[73] Assignee: UOP LLC, Des Plaines, Ill.

[21] Appl. No.: 09/336,845

[22] Filed: Jun. 21, 1999

Related U.S. Application Data

[63] Continuation-in-part of application No. 08/841,982, Apr. 8, 1997, Pat. No. 5,962,759, which is a continuation-in-part of application No. 08/600,213, Feb. 12, 1996, abandoned.

[51] Int. Cl.[7] .................................................. C07C 2/66
[52] U.S. Cl. ........................................ 585/467; 585/446
[58] Field of Search ...................................... 585/467, 446

[56] References Cited

U.S. PATENT DOCUMENTS

| | | | |
|---|---|---|---|
| 4,876,408 | 10/1989 | Ratcliffe et al. | 585/467 |
| 4,891,458 | 1/1990 | Innes et al. | 585/223 |
| 4,973,780 | 11/1990 | Johnson et al. | 585/446 |
| 5,081,323 | 1/1992 | Innes et al. | 585/449 |
| 5,087,784 | 2/1992 | Primack et al. | 585/446 |
| 5,227,558 | 7/1993 | Shamshoum et al. | 585/446 |
| 5,324,877 | 6/1994 | West et al. | 585/467 |
| 5,723,710 | 3/1998 | Gajda et al. | 585/467 |
| 5,962,759 | 10/1999 | Gajda | 585/467 |

*Primary Examiner*—Walter D. Griffin
*Assistant Examiner*—Nadine Preisch
*Attorney, Agent, or Firm*—John G. Tolomei; Frank S. Molinaro

[57] ABSTRACT

Reduction of the amount of 1,1-diphenylethane and heavier polyalkylated benzenes produced in the formation of ethylbenzene by alkylation of benzene with ethylene can be effected by reducing the number of hydride transfer active sites on a zeolite beta. One way of producing this "site-modified" beta is to take a parent or precursor zeolite beta that has at least 0.5% carbon on it and treat it under oxidation conditions at a temperature of about 450° C. to about 750° C. The use of such a catalyst gives a product containing less than 0.3 wt. % 1,1-diphenylethane relative to ethylbenzene.

10 Claims, No Drawings

MINIMIZING DIPHENYLETHANE FORMATION IN ALKYLATION OF BENZENE BY ETHYLENE CATALYZED BY ZEOLITE BETA

CROSS REFERENCE TO RELATED APPLICATION

This application is a continuation-in-part of U.S. application Ser. No. 08/841,982 filed on Apr. 8, 1997 now U.S. Pat. No. 5,962,759 which in turn is a continuation-in-part of U.S. application Ser. No. 08/600,213, filed Feb. 12, 1996, now abandoned, all of which are incorporated by reference.

BACKGROUND OF THE INVENTION

This application relates to a new form of zeolite beta and to its use as a catalyst in the alkylation of aromatic compounds. More particularly, this application relates to a zeolite beta which shows substantially greater selectivity when used in the alkylation of benzene by ethylene. It is contemplated that the catalyst of this invention will be particularly valuable in production of high purity ethylbenzene, in minimizing formation of the diphenylethane which accompanies benzene alkylation by ethylene and in maximizing benzene utilization.

Ethylbenzene is the major article of commerce which is commonly made by the alkylation of benzene with ethylene. As is usual, several byproducts accompany ethylbenzene formation; a simplified summary of alkylation processes and products commonly occurring are given below.

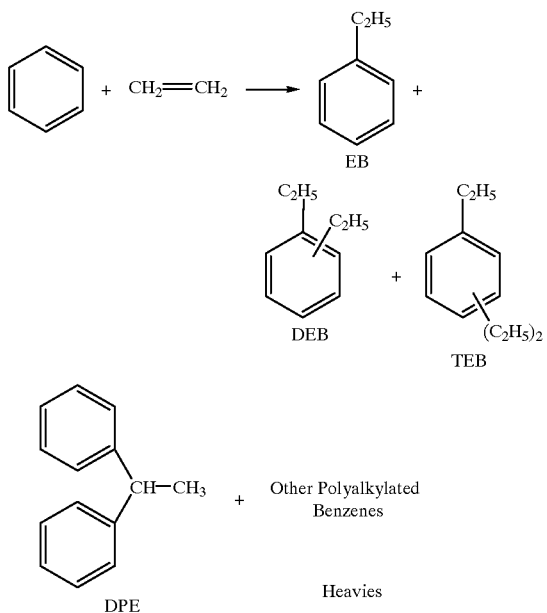

Zeolite beta has been found to be an effective catalyst and has gained a prominent role in the alkylation of benzene by ethylene. Although the formation of isomeric diethylbenzenes and triethylbenzenes might, at first glance, be viewed as byproducts representing a loss of ethylene, hence a reduction in efficiency of ethylene utilization, in fact each can be readily transalkylated to afford ethylbenzene as the sole alkylated benzene.

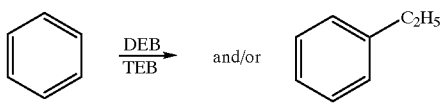

In contrast, diphenylethane can not be converted to ethylbenzene via alkylation and thus represents a loss of ethylene and a reduction in ethylene utilization efficiency. In fact, the coproduction of diphenylethane and polyalkylated benzenes, where the latter are collectively known as heavies, represents virtually all of the reduction in ethylene utilization.

Where Y zeolite is used as a catalyst in the reaction of ethylene and benzene approximately 0.65% DPE and about 0.55 weight percent of heavies are formed, resulting in a total loss of about 1.2%. Where zeolite beta is used only about 0.4% DPE and about 0.1% heavies are formed, resulting in a loss of 0.5%. Although this improvement is small it also is very significant, resulting in zeolite beta gaining favor as a catalyst of choice for ethylbenzene production. However, formation of even the latter small amount of DPE and heavies is vexing and gave impetus to further research whose goal was to reduce losses still further.

Applicant has found that by reducing the number of active sites (on zeolite beta) which catalyze hydride transfer reaction, one obtains a product (from the alkylation of benzene) with a significant reduction in DPE content. One can modify or reduce the number of hydride transfer active ways in a number of ways such as subjecting the zeolite beta to a carbon burn or calcining the zeolite beta for an extended time in a steam atmosphere at temperatures greater than 675° C.

U.S. Pat. No. 4,876,408 discloses the use of a carbon burn to modify zeolites, including zeolite beta, in order to increase it selectively for monoalkylation by at least 1.0 percentage point. In contrast to the '408 reference, the site-modified zeolite beta of this invention decreases monoalkylation selectivity, a result which is certainly unexpected in view of the contrary prior art teaching! It also is not obvious that a decrease in monoalkylation would be desirable, or even tolerable.

U.S. Pat. No. 5,227,558 discloses a steam modified zeolite beta for aromatic alkylation. However, the '558 patent discloses that the steaming dealuminates the zeolite to give a $SiO_2/Al_2O_3$ ratio between about 50 and 350. In contrast, applicant's zeolite beta has a $SiO_2/Al_2O_3$ ratio of 30 or less.

SUMMARY OF THE INVENTION

The instant invention relates generally to a process for producing monoalkylated benzene. Accordingly, one embodiment of the invention is a process for preparing a monoalkylated benzene comprising alkylating benzene with an olefin in a molar ratio from 1 up to about 15 at a temperature from about 100° C. up to about 425° C. and at a pressure sufficient to maintain at least a partial liquid phase in the presence of a site-modified zeolite beta catalyst, which has a reduced number of hydride transfer active sites versus a parent zeolite beta, the catalyst further characterized in that it produces a monoalkylated benzene product containing less than 0.3 weight percent diphenylalkane relative to the monoalkylbenzene and containing dialkylbenzenes having a meta: para ratio greater than 1.25.

DETAILED DESCRIPTION OF THE INVENTION

In the alkylation of benzene with ethylene, using a zeolite beta catalyst to form ethylbenzene, the formation of both 1,1-diphenylethane (DPE) and polyalkylated materials (heavies) which cannot be transalkylated with benzene to afford ethylbenzene, represent small but significant loss of ethylbenzene production. Without wishing to be bound by any one particular theory, the formation of DPE probably results from hydride transfer in chemisorbed ethylbenzene to ethylene with formation of chemisorbed styrene which then serves to alkylate benzene. This is summarized in the following reaction.

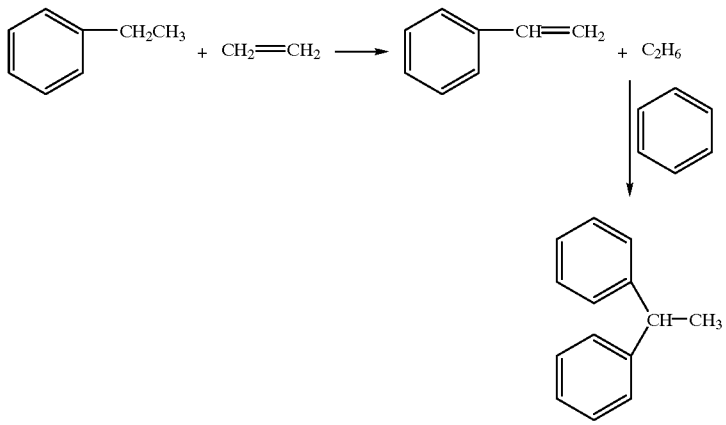

It is known that the amount of DPE formed depends on the ethylene (E):benzene (B) ratio according to the formula $$[DPE] \approx [E/B]^2$$

Thus, increasing this ratio (or conversely, decreasing the B/E ratio, since the reaction typically is run at B/E>>1) increases the amount of DPE formed, which is undesirable. However, it is preferred to carry out the reaction at as high a ratio of ethylene to benzene to reduce the utilities cost associated with the recovery of excess benzene, which conflicts directly with the desire to minimize DPE production. Thus, it is doubly imperative to increase the selectivity—as measured by DPE and heavies production—of a zeolite beta catalyst.

By reducing the number of hydride transfer active sites on a zeolite beta, one obtains a lower production of DPE. In fact, the level of DPE formed during alkylation of benzene is a direct measure of the number of hydride transfer active sites on the zeolite beta. Thus, one can measure the amount of DPE formed before and after certain treatments have been carried out on the zeolite beta to determine whether the number of hydride transfer sites has been reduced or not. Therefore, for the purposes of this invention, a zeolite beta which has a reduced number of hydride transfer sites versus a parent zeolite beta will be termed a site-modified zeolite beta.

Applicant has found two ways in which to decrease the number of hydride transfer active sites. The first way is to take a non-templated zeolite which contains at least 0.5% carbon and preferably at least 1% carbon and which has been subjected to a carbon burn or carbon burn conditions. What is meant by the phrase "1% carbon on the catalyst" is that there is 1 weight percent carbon on the catalyst as determined by combustion analysis to generate CO and $CO_2$ using a LECO analyzer. One way (and perhaps the easiest) to deposit the carbon on the zeolite beta is to use a zeolite beta catalyst which has undergone considerable process use. During use, the catalyst can accumulate from about 0.5 to about 10 weight percent carbon and more usually from about 1 up to about 5 weight percent carbon. The form of the carbon includes light and heavy molecular weight organic compounds as well as coke. As a preliminary step, the catalyst is washed with benzene for 24 hours at about 200° C. to about 250° C. However, any aromatic compound capable of entering the zeolite beta channels may be used as a wash solvent, and the wash solvent also may contain up to about 30 weight percent of saturated hydrocarbons. This wash removes all lighter materials so that only coke and higher molecular weight organic materials remain in the pores. Such higher molecular weight organic materials include polyalkylated compounds and ethylene oligomers. This precursor or parent non-templated zeolite beta is then subject to thermal oxidation. Such conditions include a temperature between about 450° C. and 750° C., preferably between 600° C. and 700° C. for a time between about 1 and about 10 hrs. in an oxidative atmosphere. Any atmosphere containing at least 0.5% oxygen can be used with air being the most convenient and usual. The oxidation normally is performed with air flowing over the zeolite beta at a rate between 10 and 1000 SCFH/percent of catalyst (measured on a volatile-free basis), with rates of 20–30 SCFH/percent catalyst usually being sufficient. It is critical to note that the catalysts, prepared according to the foregoing method, do not afford an increase in monoalkylation selectivity, but in fact effect alkylation with decreased monoalkylation selectivity.

Another method of making the site-modified zeolite beta of this invention is to calcine a zeolite beta, templated or not, for extended times at over 675° C. up to about 850° C. in a steam atmosphere. More specifically, a calcination time of at least 6 hours is necessary at temperatures below 700° C. although as the temperature increases to 750° C. the calcination time may be decreased to about 3 hours. It is important that the calcination be done in a steam atmosphere, especially in an atmosphere containing from about 5 up to about 25 weight percent water. The resulting steam calcined zeolite beta has a silica to alumina ratio which is no greater than about 30.

It should be pointed out that these two procedures are not the only means by which the number of hydride transfer active sites can be reduced. Other means can be derived by one of ordinary skill in the art from the information provided herein.

As stated, the instant invention is particularly applicable to the liquid phase alkylation of benzene with ethylene. The molar ratio of benzene to ethylene is in the range of 8:1 to about 1:1, although the alkylation is more generally performed at a molar ratio between about 6:1 to as low as 3:1. As stated previously, a lower ratio is desirable from the aspect of lowering utilities cost, but is undesirable in that it leads to more DPE formation. However, as discussed above our invention can be expected to be generally applicable to the alkylation of aromatics with olefins. Although benzene is the principal aromatic compound of interest, aromatics such as alkyl-substituted benzenes, condensed ring systems generally and alkylated derivatives thereof may be used. Exemplary of such materials are toluene, ethylbenzene, propylbenzene, and so forth; xylene, mesitylene, methylethylbenzene and so on; naphthalene, anthracene, phenanthrene, methylnaphthalene, dimethyinaphthalene, and tetralin. Although the lower olefins, i.e., those having 2–6 carbon atoms, are the principal alkylating agents contemplated olefins in the C2–C20 range may be effectively used in the practice of our invention. In general, the molar ratio of olefin to aromatic is within the range of 15:1 to about 1:1, and generally is under about 8:1.

The alkylation is performed in the liquid phase. Consequently, reaction pressures need to be sufficiently high to ensure at least a partial liquid phase. A pressure between about 200 and 1,000 psig (1379–6985 kPa) constitutes the usual pressure interval under which alkylation is run, where ethylene is the olefin, although more commonly it is carried out at a pressure between 300 and 600 psig (2069–4137 kPa), with the range between 450 and 600 psig (3103–4137 kPa) even more commonly used. However, it needs to be emphasized that pressure is not a critical variable in the success of our invention and the only criterion is that the pressure be sufficiently great to ensure at least partial liquid phase. In the general case our invention may be practiced at a pressure between about 50 psig (345 kPa) and 1000 psig. The alkylation reaction between benzene and ethylene typically is performed at a temperature between about 200° C. and about 260° C., more preferably in the interval 230–250° C., and at a liquid hourly space velocity, based on ethylene, between about 0.1 and about 1.5 per hour. For other olefins the appropriate reaction temperature is in the range 100–425° C.

As stated previously, in the alkylation of benzene with ethylene using the instant site-modified zeolite beta as catalyst there is a significant reduction in the amount of 1,1-diphenylethane and polyalkylated benzenes ("heavies") formed as byproducts which cannot be transalkylated to ethylbenzene. In particular, the present process affords less than 0.3 weight percent of the 1,1-diphenylethane plus heavies relative to ethylbenzene, which is an important improvement over prior art results. Another critical feature of the present catalysts is that there is decreased selectivity with respect to monoalkylation. Another characteristic of the site modified zeolite beta catalysts of our invention is that in the alkylation of benzene with ethylene, the diethylbenzenes are formed with a meta:para ratio greater than 1.25, preferably greater than 1.5, and most preferably greater than 1.8. In a particularly desirable variant, the ortho:para ratio is less than 0.75, preferably under 0.6, and most preferably less than 0.5. In general, alkylation of benzene by olefins using as a catalyst the site-modified zeolite beta of our invention affords dialkylbenzenes having a meta:para ratio greater than 1.25, and in a desirable variant an ortho:para ratio less than 0.75.

The alkylation of aromatics by olefins catalyzed by the catalyst of this invention may be carried out in any of the ways which are well known to those practicing the art. For example, the process in general can be carried out in a batch mode by heating the catalyst, an aromatic compound represented by benzene, and an olefin such as ethylene in a stirred autoclave at a temperature between about 200° C. and 260° C. and at a pressure sufficient to maintain at least a partial liquid phase. The pressure typically will be in the range of 200 to about 1,000 psig, but again it should be emphasized that the pressure requirements are not restrictive but serve only to ensure at least partial liquid phase reaction.

However, the process is more advantageously performed in a continuous mode employing a fixed bed reactor operating in an upflow or downflow mode or using a moving bed reactor operating with cocurrent or countercurrent catalyst and hydrocarbon flows. The reactors also may contain one or more catalyst beds and may be equipped for the interstage addition of olefin as well as interstage cooling. Interstage olefin addition assures a more nearly isothermal operation and tends to enhance product quality and catalyst life. A moving bed reactor provides the advantage of continuous spent catalyst removal for regeneration and replacement by fresh or regenerated catalyst. However, it also is possible to carry out the present invention using swing bed reactors. As yet another common variant which may be used in the practice of the invention may be mentioned effluent recycle. Thus, effluent may be recycled and mixed with fresh feed in order to ensure efficient utilization of reactants without the necessity of their separation from the reactor effluent.

The following examples are presented in illustration of this invention and are not intended as undue limitations on the generally broad scope of the invention as set out in the appended claims.

EXAMPLES

Preparation of zeolite betas. Zeolite beta was prepared in accord with the description in U.S. Pat. No. 5,139,759. Powdered zeolite beta was washed using as the wash solution an aqueous solution containing 1.0 lbs. $NH_4NO_3$ and 0.252 lbs. $HNO_3$ per pound dry weight of zeolite. The mixture of beta and wash solution were held at 85° C. for 1 hour. Solid was separated, washed well with water, air dried overnight, then dried at 200° F. (93° C.) to equilibrium. The dried zeolite was used as an extrudate which was calcined at a maximum bed temperature of 675° C. for about 3 hours. This material is designated as catalyst A in the table below.

The foregoing material was utilized as a catalyst in the alkylation of benzene by ethylene. After service it was washed with flowing benzene at 4 LHSV at 240° C. for 24 hours. The cooled catalyst was purged with hydrogen to remove residual benzene, then carbon-burned by ramping from ambient temperature to 650° C. C in 3 hours; holding at 650° C. for 3 hours, then cooled to room temperature to afford catalyst B. Air was flowing over the catalyst at ambient pressure at a rate of ca. 5 standard liters per minute.

Alkylation of benzene with ethylene using zeolite betas. Approximately 20 g of catalyst was loaded into a ⅝" ID reactor and sand-packed to minimize channeling. Feeds were passed upflow through the reactor and a reactor effluent recycle ratio of 3:1 (recycle rate relative to total benzene feed rate) was used to control the size of the exotherm. All of the olefin was mixed with the feed benzene at the reactor inlet. Other operating conditions are given in the Table.

The following table summarizes the results observed after the reactor had lined out and stabilized, i.e., after a steady state had been reached.

TABLE 1

Comparison of Original and Treated Catalysts

| Catalyst | A | B |
| --- | --- | --- |
| Temp, C. | 240.7 | 241.8 |
| Benzene LHSV | 2.9 | 3.3 |
| Pressure, psig | 549 | 545 |
| Benzene/Ethylene (molar) | 4.59 | 4.43 |
| Selectivities, % | | |
| Ethylbenzene | 89.08 | 84.77 |
| m-DEB | 6.08 | 7.97 |
| p-DEB | 2.80 | 3.82 |
| o-DEB | 0.59 | 1.64 |
| TEB | 0.94 | 1.62 |
| DPE | 0.31 | 0.13 |
| Heavies | 0.19 | 0.03 |
| Others | 0.01 | 0.02 |
| DPE/EB, % | 0.347 | 0.156 |
| C2 = Efficiency, % | 99.38 | 99.72 |

I claim as my invention:

1. A process for preparing a monoalkylated benzene comprising alkylating benzene with an olefin in a molar ratio from 1 up to about at a temperature from about 100° C. up to about 425° C. and at a pressure sufficient to maintain at least a partial liquid phase, in the presence of a zeolite beta catalyst, characterized in that the catalyst has a reduced number of hydride transfer active sites versus a parent zeolite beta as determined by the amount of diphenylalkane produced, said amount being less than 0.3 weight percent diphenylalkane relative to the amount of monoalkylbenzene produced and producing dialkylbenzenes in a meta:para ratio of greater than 1.25.

2. The process of claim 1 where the olefin has from 2 up to about 20 carbon atoms.

3. The process of claim 2 where the olefin has from 2 up to about 6 carbon atoms.

4. The process of claim 1 where the molar ratio of benzene to olefin is between about 1 and about 8.

5. The process of claim 1 where the pressure is from about 450 to about 600 psig.

6. The process of claim 1 further characterized in that the dialkylbenzenes have an ortho:para ratio less than 0.75.

7. A process for making ethylbenzene comprising alkylating benzene with ethylene in a molar ratio from 1 up to about 8 at a temperature from about 200° C. up to about 260° C. and at a pressure sufficient to maintain at least a partial liquid phase, in the presence of a zeolite beta catalyst, characterized in that the catalyst has a reduced number of hydride transfer active sites versus a parent zeolite beta as determined by the amount of 1,1-diphenylethane produced, said amount of being less than 0.3 weight percent, 1,1-diphenylethane relate to the amount of ethylbenzene and producing diethylbenzenes in a meta:para ratio of greater than 1.25.

8. The process of claim 7 where the molar ratio of benzene to ethylene is between about 3 and about 6.

9. The process of claim 7 where the reaction temperature is from about 230° C. to about 250° C.

10. The process of claim 7 where the pressure is from about 450 to about 600 psig.

* * * * *